(12) United States Patent
Brooks et al.

(10) Patent No.: US 8,968,391 B2
(45) Date of Patent: Mar. 3, 2015

(54) SYSTEMS AND METHODS TO REDUCE GEL RETRACTION

(75) Inventors: Dennis Brooks, Windsor, CA (US); Jack Chu, Santa Rosa, CA (US); Scott Doig, Santa Rosa, CA (US); Trevor Huang, Maple Grove, MN (US); Tessy Kanayinkal, Brooklyn Park, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 2194 days.

(21) Appl. No.: 11/685,257

(22) Filed: Mar. 13, 2007

(65) Prior Publication Data
US 2007/0202093 A1 Aug. 30, 2007

Related U.S. Application Data

(63) Continuation-in-part of application No. 10/977,545, filed on Oct. 28, 2004, now abandoned.

(51) Int. Cl.
| | | |
|---|---|---|
| *A01N 1/02* | (2006.01) | |
| *A61K 38/48* | (2006.01) | |
| *A61F 2/06* | (2013.01) | |
| *A01N 65/00* | (2009.01) | |
| *A61L 27/36* | (2006.01) | |
| *A61L 27/54* | (2006.01) | |

(52) U.S. Cl.
CPC .......... *A61L 27/3616* (2013.01); *A61L 27/3641* (2013.01); *A61L 27/3645* (2013.01); *A61L 27/54* (2013.01); *A61L 2300/414* (2013.01)
USPC .......... 623/1.41; 435/2; 424/94.64; 424/93.72

(58) Field of Classification Search
None
See application file for complete search history.

(56) References Cited

U.S. PATENT DOCUMENTS

| | | | | |
|---|---|---|---|---|
| 2001/0055621 | A1* | 12/2001 | Baugh et al. | 424/530 |
| 2004/0197319 | A1* | 10/2004 | Harch et al. | 424/93.72 |

OTHER PUBLICATIONS

Barry L. Eppley et al. "Platelet Quantification and Growth Factor Analysis from Platelet-Rich Plasma: Implications for Wound Healing" Plast. Reconstr. Surg. 114: 1502, 2004.*
Loose et al. "The Managment of peripheral arterial aneurysms using percutaneous injection of fibrin adhesive" British J. of Radiology 71 (1998) 1255-1259.*
Didier Sirieix et al. "Comparative Study of Different Biological Glues in an Experimental Model of Surgical Bleeding in Anesthetized Rats: Platelet-Rich and -Poor Plasma-Based Glue with and without Aprotinin versus Commercial Fibrinogen-Based Glue" Annals of Vascular Surgery vol. 12, No. 4, 1998, 311-316.*
Aventis Behring "Beriplast® P Combi-Set 1 ml" 2 pgs, updated Dec. 2000.*
Mok et al. "Combined endovascular stent grafting and endoscopic injection of fibrin sealant for aortoenteric fistula complicating esophagectomy" Journal of Vascular Surgery vol. 40, No. 6, pp. 1234-1237.*

* cited by examiner

*Primary Examiner* — Thane Underdahl

(57) ABSTRACT

Methods for ameliorating stent graft migration and endoleak using treatment site-specific cell growth promoting compositions in combination with stent grafts are disclosed. Also disclosed are application of cell growth promoting compositions such as, but not limited to, autologous platelet gel compositions directly to treatment sites during or after stent graft implantation.

4 Claims, 14 Drawing Sheets

FIG. 12a
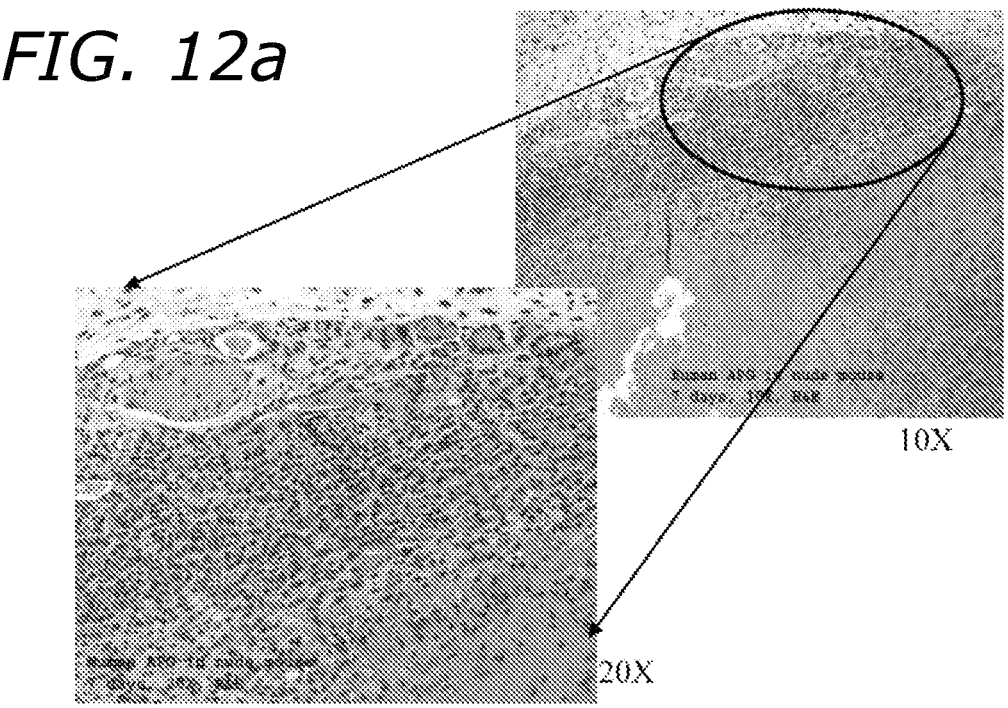
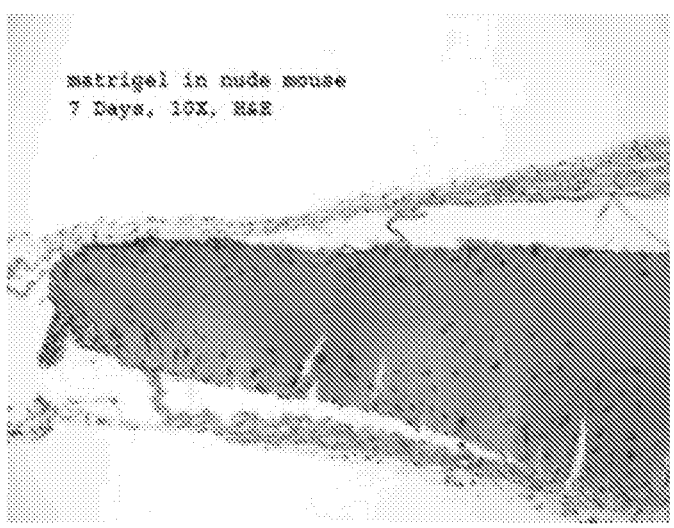
FIG. 12b

SYSTEMS AND METHODS TO REDUCE GEL RETRACTION

CROSS REFERENCE TO RELATED APPLICATIONS

This application is a continuation-in-part of U.S. patent application Ser. No. 10/977,545 filed Oct. 28, 2004 now abandoned which is incorporated by reference herein in its entirety.

FIELD OF THE INVENTION

Methods for reducing the risk of stent graft migration and endoleak are disclosed. Specifically, methods for applying cell growth promoting compositions such as, but not limited to, autologous platelet gel compositions directly to treatment sites before, during or after stent graft implantation are provided.

BACKGROUND OF THE INVENTION

An aneurysm is a localized dilation of a blood vessel wall usually caused by degeneration of the vessel wall. These weakened sections of vessel walls can burst, causing an estimated 32,000 deaths in the United States each year. Additionally, aneurysm deaths are suspected of being underreported because sudden unexplained deaths, about 450,000 in the United States alone, are often simply misdiagnosed as heart attacks or strokes while many of them may be due to aneurysms.

U.S. surgeons treat approximately 50,000 abdominal aortic aneurysms each year, typically by replacing the abnormal section of vessel with a polymer graft in an open surgical procedure. A less-invasive procedure that has more recently been used is the placement of a stent graft at the aneurysm site. Stent grafts are tubular devices that span the aneurysm site to provide support without replacing a section of the vessel. The stent graft, when placed within a vessel at an aneurysm site, acts as a barrier between blood flow and the weakened wall of a vessel, thereby decreasing pressure on the damaged portion of the vessel. Patients whose multiple medical comorbidities make them very high risk for conventional aneurysm repair can be candidates for stent grafting.

While stent grafts can represent improvements over previously-used vessel treatment options, there are still risks associated with their use. The most common of these risks is migration of the stent graft due to matrix remodeling and/or hemodynamic forces within the vessel. Stent graft migration can lead to endoleaks, i.e., the leaking of blood into the aneurysm sac between the outer surface of the graft and the inner lumen of the blood vessel, which can increase the risk of vessel rupture. Such migration of stent grafts is especially possible in curved portions of vessels where asymmetrical forces place uneven forces on the stent graft.

Based on the foregoing, one goal of treating aneurysms is to provide stent grafts that do not migrate. To achieve this goal, stent grafts with stainless steel anchoring barbs that engage the vessel wall have been developed. Additionally, endostaples that fix stent grafts more securely to the vessel wall have been developed. While these physical anchoring devices have proven to be effective in some patients, they have not sufficiently ameliorated stent graft migration associated with current treatment methods in all cases.

An additional way to reduce the risk of stent graft migration is to administer to the treatment site, either before, during or relatively soon after implantation, one or more growth factors. The administration of one or more growth factors can be beneficial because, normally, the material of the stent graft does not provide a hospitable environment for cells in the area to grow. As a result, the stent graft rests against the vessel wall and may not be incorporated into the vessel wall. If one or more growth factors are administered immediately before, during or relatively soon after stent graft deployment and implantation, the smooth muscle cells and fibroblasts will be stimulated to proliferate. As these cells proliferate they can grow around the stent graft such that the device becomes physically attached to the vessel wall rather than merely resting against it.

Co-pending U.S. patent application Ser. No. 10/977,545, to which this application claims priority and which is fully incorporated by reference herein, describes promoting cell growth with autologous platelet gel (APG). This method provides numerous benefits that reduce the overall likelihood of stent graft migration and endoleak. It has been noted, however, that in some instances, after application at an aneurysm treatment site, the APG can retract from its original deposition volume. Thus, while the risk of stent graft migration and endoleak is reduced overall, when this retraction occurs, a small potential for endoleak is re-created. Thus, there is room for further improvement in administering APG at aneurysm sites to even further reduce the risk of endoleak. Embodiments according to the present invention address this opportunity by providing methods to reduce the likelihood of APG retraction at aneurysm sites.

SUMMARY OF THE INVENTION

Administering autologous platelet gel (APG) at aneurysm treatment sites where stent grafts are deployed can stimulate cell growth around the stent graft and reduce the overall likelihood of stent graft migration and resulting endoleak. In some instances, however, APG can retract after it is administered at a treatment site. When this retraction occurs, a small potential for endoleak is created. Embodiments according to the present invention address this potential by providing methods to reduce the likelihood of APG retraction at aneurysm sites.

Reducing the likelihood of APG retraction at an aneurysm site can be achieved with several different methods. One non-limiting method includes (1) mixing platelet rich plasma (PRP) with thrombin to form a gel; (2) once the gel retracts, collecting the growth factor rich exudate from the retracted gel (3) mixing the collected growth factor rich exudate with platelet poor plasma (PPP); and (4) injecting this mixture and thrombin into the aneurysm sac approximately simultaneously to form a gel. The gel formed according to this method has concentrated growth factors with little to no retraction.

In another embodiment of the methods according to the present invention, the method comprises the steps of (1) obtaining autologous PRP; (2) activating the platelets in the autologous PRP with a strong platelet agonist to cause alpha granule secretion which will lead to the secretion growth factors wherein the strong platelet agonists can include, without limitation, adenosine diphosphate and thrombin receptor activating peptide; (3) centrifuging the activated plasma to remove activated and spent platelets and platelet debris (i.e. micro-particles); (4) mixing the activated plasma with PPP; and (5) injecting the mixture with thrombin into the aneurysm sac to form a gel. This injected gel is rich in growth factors resulting in little to no gel retraction.

In another embodiment of the methods according to the present invention, the method comprises the steps of (1)

obtaining autologous PRP; (2) mixing the PRP with a biocompatible material such as, without limitation, hyaluronic acid, alginate, collagen, fibrin/fibrinogen, dextran, β-cyclodextrin, polyvinyl alcohol or hydrogel; (3) injecting the mixture into the aneurysm sac; and (4) activating the platelets in the sac by injecting thrombin to form a gel. Alternatively, the PRP/biocompatible gel mixture and thrombin can be injected (delivered) into the aneurysm sac simultaneously to form a gel. Additionally, in one embodiment, clotting factor XIII can be added to enhance cross-linking of the fibrin matrix formed upon the addition of thrombin to further strengthen the formed clot.

The presently described methods can enhance the strength and durability of APG as a sac filler; can enhance the dimensional stability of APG to reduce the risk of sac remodeling; can enhance tissue repair; and can enhance the adhesion of the APG to the sac wall to further reduce the risk of stent graft migration and endoleak.

BRIEF DESCRIPTION OF THE DRAWINGS

FIGS. 12a-b depict the tissue response to implantation of the APG or Matrigel® substrate in athymic mice.

DEFINITION OF TERMS

Figure 1:
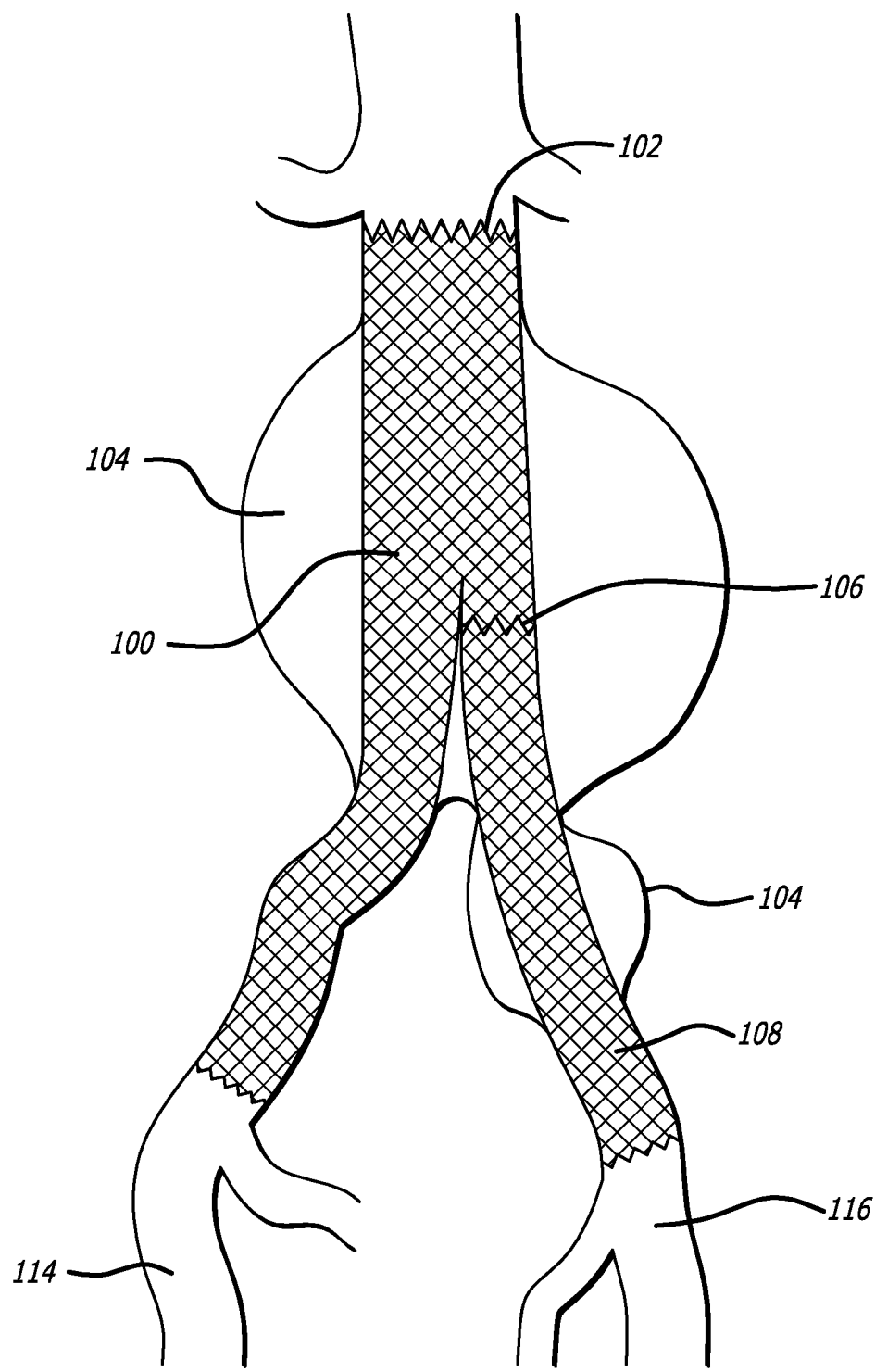
FIG. 1 depicts a fully deployed stent graft with a schematicized exterior metal scaffolding as used in one embodiment according to the present invention.

Prior to setting forth embodiments according to the present invention, it may be helpful to an understanding thereof to set forth definitions of certain terms that will be used hereinafter:

Animal: As used herein "animal" shall include mammals, fish, reptiles and birds. Mammals include, but are not limited to, primates, including humans, dogs, cats, goats, sheep, rabbits, pigs, rodents, horses and cows.

Biocompatible: As used herein "biocompatible" shall mean any material that does not cause injury or death to the animal or induce an adverse reaction in an animal when placed in intimate contact with the animal's tissues. Adverse reactions include inflammation, infection, fibrotic tissue formation, cell death, or thrombosis.

Cell Growth Promoting Compositions: As used herein "cell growth promoting factors" or "cell growth promoting compositions" shall include any bioactive compound having a growth promoting effect on vascular cells. Exemplary, non limiting examples include, vascular endothelial growth factor (VEGF), platelet-derived growth factor (PDGF), platelet-derived epidermal growth factor (PDEGF), fibroblast growth factors (FGFs), transforming growth factor-beta (TGF-β), platelet-derived angiogenesis growth factor (PDAF) and autologous platelet gel (APG).

Drug(s): As used herein "drug" shall include any bioactive compound or composition having a therapeutic effect in an animal. Exemplary, non limiting examples include small molecules, peptides, proteins, hormones, DNA or RNA fragments, genes, cells, genetically-modified cells, cell growth promoting compositions, matrix metalloproteinase inhibitors and autologous platelet gel (APG).

Endoleak: As used herein "endoleak" refers to the presence of blood flow between the end of a stent graft and a vessel wall into an aneurysm sac, when all such flow should be contained within the stent graft's lumen (commonly referred to as a Type I endoleak).

Heparin Binding Growth Factor Family: As used herein "heparin binding growth factor family shall include factors binding heparin and having a positive growth effect on vascular cells. Exemplary, non limiting examples include fibroblast growth factor 1 (FGF-1), FGF-2 and insulin-like growth factor.

Migration: As used herein "migration" refers to displacement of the stent graft sufficient to be associated with another complication, for example, endoleak.

Simultaneous: As used herein, "simultaneous" or "simultaneously" refers to events that occur approximately coincident, that is, at approximately the same time.

Treatment Site: As used herein "treatment site" shall mean an aneurysm site, acute traumatic aortic injury or other vascular-associated pathology.

Vascular Growth Factor: As used herein "vascular growth factor" shall include factors having a positive effect on growth of vascular cells. Exemplary, non limiting examples include vascular endothelial growth factor A (VEGF-A), VEGF-B, VEGF-C, VEGF-D and placental growth factor.

DETAILED DESCRIPTION

Embodiments according to the present invention provide compositions, devices and related methods useful for reducing the risk of implantable medical device post-implantation migration and endoleak. More specifically, the compositions, devices and related methods promote implantable medical device attachment to blood vessel luminal walls. One embodiment provides methods and compositions useful for minimizing post-implantation stent graft migration following deployment at an aneurysmal treatment site and is also useful in preventing or minimizing post-implantation endoleak following stent-graft deployment at an aneurysmal treatment site.

For convenience, the devices, compositions and related methods according to the present invention discussed hereinafter will be exemplified using stent grafts intended to treat aneurysms. As discussed briefly above, an aneurysm is a swelling, or expansion of a blood vessel lumen at a defined point and is generally associated with a vessel wall defect.

Aneurysms are often a multi-factorial asymptomatic vessel disease that if left unchecked may result in spontaneous rupture, often with fatal consequences. Previous methods to treat aneurysms involved highly invasive surgical procedures where the affected vessel region was removed (or opened) and replaced (or supplemented internally) with a synthetic graft that was sutured in place. However, this procedure requires the patient to be healthy enough to undergo this highly invasive procedure usually including a several week hospital stay and is therefore considered risky and not appropriate for all patients. Patients who because of their poor health were not candidates for this procedure remained untreated and thus at continued risk for sudden death.

To overcome the risks associated with invasive aneurysmal surgeries, stent grafts were developed. Stent grafts can be positioned and deployed using minimally invasive procedures. Essentially, a catheter having a stent graft compressed and fitted into the catheter's distal tip is advanced through an artery to a position spanning the aneurysmal site. The stent graft is then deployed within the vessel lumen juxtaposed to the weakened vessel wall forming an inner liner that insulates the aneurysm from the body's hemodynamic forces thereby reducing, or eliminating the possibility of rupture. The size and shape of the stent graft is matched to the treatment site's lumen diameter and aneurysm length.

Stent grafts generally comprise a metal scaffolding having a biocompatible graft material lining or covering such a Dacron®, ePTFE, or a fabric-like material woven from a variety of biocompatible polymer fibers. The scaffolding in some embodiments is disposed on the luminal wall-contacting surface of the stent graft and directly contacts the vessel lumen. The graft material is stitched, glued or molded to the scaffold. The scaffolding may be on the graft's blood flow contacting surface or interior. When a self-expanding stent graft is deployed from the delivery catheter, the scaffolding expands the graft material to fill the lumen and exerts radial force against the lumen wall. This radial force is generally sufficient to keep the stent-graft from migrating and to minimize endoleak. However, stent migration and endoleak may occur in vessels that have irregular shapes or are shaped such that they exacerbate hemodynamic forces within the lumen. Stent graft migration refers to a stent graft moving from the original deployment site, usually in the direction of the blood flow. Endoleak (Type I) refers to the leakage of blood through the seal between the stent graft and the surrounding luminal wall at the ends of the stent graft into the aneurysm sac. This leakage can result in the aneurysm sac continuing to be subjected to systemic blood pressure again, thus increasing the risk of rupture. It would be beneficial to have devices, compositions and methods that reduce the risk of post implantation stent graft migration and endoleak.

The vessel wall's blood-contacting lumen surface is a layer of endothelial cells. In the normal mature vessel the endothelial cells are quiescent and do not multiply. Thus, a stent graft carefully placed against the vessel wall's blood-contacting luminal surface rests against a quiescent endothelial cell layer. However, if cell growth promoting compositions are administered immediately before, during or immediately after stent graft deployment, the normally quiescent endothelial cells lining the vessel wall, and in intimate contact with the stent graft luminal wall contacting surface, will be stimulated to proliferate. The same will occur with smooth muscle cells and fibroblasts found within the vessel wall. As these cells proliferate they will grow into and around the stent graft lining such that the stent graft becomes physically attached to the vessel lumen rather than merely resting against it. In one embodiment according to the present invention, the stent graft has a metallic scaffolding on the graft's luminal wall contacting surface and the cell growth promoting factor is autologous platelet gel (APG).

Autologous platelet gel is formed from autologous platelet rich plasma (PRP) mixed with thrombin and calcium. The PRP is generated from variable speed centrifugation of autologous blood using devices such as, but not limited to the Magellan® Autologous Platelet Separation System (Medtronic Inc., Minneapolis, Minn.). The PRP contains sufficient fibrinogen to allow a fibrin gel to form when mixed with calcium and thrombin. In addition, the PRP contains a high concentration of platelets that can aggregate for plugging, as well as release cytokines, growth factors or enzymes following activation by thrombin. Some of the many factors released by the platelets and the white blood cells present that constitute the PRP include platelet-derived growth factor (PDGF), platelet-derived epidermal growth factor (PDEGF), fibroblast growth factor (FGF), transforming growth factor-beta (TGF-β) and platelet-derived angiogenesis growth factor (PDAF). These factors have been implicated in wound healing by increasing the rate of collagen secretion, vascular in-growth and fibroblast proliferation.

Implantable medical devices, specifically stent grafts, are advantageously sealed to the vessel lumen using APG. The APG comprises platelet aggregates which help mechanically seal the stent graft to the lumen wall in addition to providing a rich source of growth factors. Briefly, following activation by thrombin, platelets release thromboxane A2, adenosine diphosphate and thrombin, factors that attract additional platelets to the developing clot. Once associated with the stent graft, APG, with its rich composition of growth and healing factors, can promote the integration of the stent graft into the vessel wall. Enhanced healing and tissue in-growth from the surrounding vessel may lessen the chances of stent graft migration and endoleak. Additionally, drugs that inhibit matrix metalloproteinases, or other pathological processes involved in aneurysm progression, can be incorporated into the gel to enhance wound healing and/or stabilize and possibly reverse the pathology. Drugs that induce positive effects at the aneurysm site can also be delivered by APG and the methods described herein.

Autologous platelet gel is not easily injectable. Therefore, it can be generated and applied to a stent graft in the operating room immediately prior to stent graft deployment. The stent graft can be coated with APG by dipping the stent in a receptacle containing the forming gel or using a modified version of a standard delivery catheter to deliver the components of the APG to the treatment site. Single lumen or multilumen catheters may be used to deliver the components of APG or to deliver the PRP and calcium/thrombin activating solution concurrently to the aneurysm site.

Because of the physical properties of APG, it may be particularly useful in promoting endothelialization of vascular stent grafts. The APG not only can coat the exterior surface of the stent graft but also fills the pores, inducing migrating cells into the stent graft fabric. As a result, engraftment of autologous endothelial cells will occur preferentially at those sites where APG was injected. Additionally the APG may fill gaps between the stent graft outer wall and the inner lumen of the healthy portion of the vessel above and below the aneurysm sac further preventing endoleaks and providing structural support for weakened arterial walls within the aneurysm sac.

One problem with the use of APG is that after the gel is formed in the sac, in some instances it can retract, potentially creating a gap between the gel and the sac wall through which endoleak can begin. Embodiments according to the present invention provide methods to reduce the occurrence of gel retraction thus further reducing the risk of endoleak. In one embodiment the method comprises the steps of (1) mixing platelet rich plasma (PRP) with thrombin to form a gel; (2) once the gel retracts, collecting the growth factor rich exudate from the retracted gel; (3) mixing the collected growth factor rich exudate with platelet poor plasma (PPP); and (4) injecting this mixture approximately simultaneously with thrombin into the aneurysm sac to form a gel. The gel formed according to this method has concentrated growth factors with little to no retraction.

In another embodiment the method comprises the steps of (1) obtaining autologous PRP from a patient's own blood through a centrifuge (e.g. a Magellan® autologous platelet separator) (this PRP is enriched in platelets (about 3 to 12 times baseline count depending on volume)); (2) activating the platelets in the autologous PRP with a strong platelet agonist to cause alpha granule secretion which will lead to the secretion of growth factors, (strong platelet agonists include, without limitation, adenosine diphosphate (ADP) at concentrations of about 5 to about 20 µM, or of about 11 to about 15 µM and thrombin receptor activating peptide (TRAP) at concentrations of about 5 to about 10 µM or of about 7 to about 8 µM); (3) centrifuging the activated plasma to remove activated and spent platelets and platelet debris (i.e. micro-particles); (4) mixing the activated plasma with PPP; and (5) injecting the mixture (along with thrombin) into the aneurysm sac to form a gel. This injected gel is rich in growth factors resulting in little to no gel retraction behavior.

In another embodiment the method comprises the steps of (1) obtaining autologous PRP from a patient's own blood; (2) mixing the PRP with a biocompatible material such as, without limitation, hyaluronic acid, alginate, collagen, fibrin/fibrinogen, dextran, β-cyclodextrin, polyvinyl alcohol or hydrogel; (3) injecting the mixture into the aneurysm sac; and (4) activating the platelets in the sac by injecting thrombin (alternatively, the PRP/biocompatible gel mixture and thrombin can be injected (delivered) into the aneurysm sac simultaneously to form a gel). Additionally, in one embodiment, clotting factor XIII can be added to enhance cross-linking of the fibrin matrix formed upon the addition of thrombin to further strengthen the formed clot.

The presently described methods can enhance the strength and durability of APG as a sac filler; can enhance the dimensional stability of APG to reduce the risk of sac remodeling; can enhance tissue repair; and can enhance the adhesion of the APG to the sac wall to further reduce the risk of stent graft migration and endoleak.

In some embodiments, a stent graft is provided "pre-loaded" into a deployment catheter and thus cannot be pre-coated with the APG mixtures of the present invention. In this situation, APG mixtures can be applied to the stent graft, luminal wall or both, during stent graft deployment. In one exemplary stent graft deployment to the site of an abdominal aneurysm, a vascular bifurcated stent graft segment 100 is fully deployed through the right iliac artery 114 to an aneurysm site 104 (FIG. 1). The bifurcated stent graft segment 100 has a proximal end 102. An iliac leg segment 108 is positioned in the left iliac artery 116 to anchor the stent graft (system) to the iliac artery. Bifurcated stent graft segment 100 is deployed first in a first deployment catheter (not shown) and iliac leg segment 108 is deployed second in a second deployment catheter (not shown). The bifurcated stent graft segment 100 and iliac leg segment 108 are joined with an overlap (located at about 106) between the two segments.

Figure 2A:
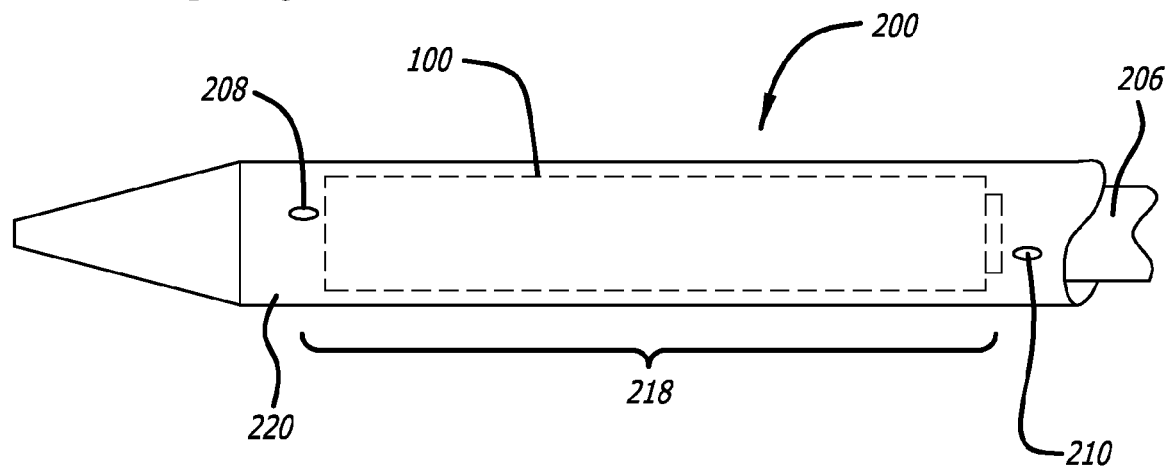
FIGS. 2a-b depict a stent graft delivery catheter containing a multilumen injection catheter for administering autologous platelet gel (APG) or other substances during stent graft deployment.
Figure 2B:
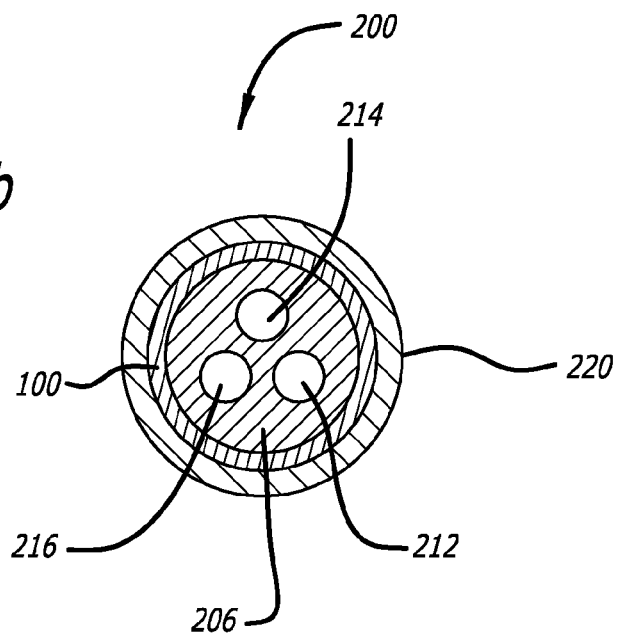

In one embodiment according to the present invention, a stent graft is pre-loaded into a delivery catheter such as that depicted in FIG. 2a. Bifurcated stent graft segment 100 is radially compressed to fill the stent graft chamber 218 in the distal end of catheter 200. The bifurcated stent graft segment 100 is covered with a retractable sheath 220. Within the lumen of catheter 200 is a multilumen injection catheter 206. Injection catheter 206 (FIG. 2b) can have a guide wire lumen 212, a lumen for delivery of PRP or other substances 214 and a lumen for delivery of thrombin or other substances 216. Catheter 206 has two injection (delivery) ports 208 and 210 (FIG. 2a) for delivering PRP and thrombin (or other cell growth promoting factors) during stent graft deployment.

Figure 3A:
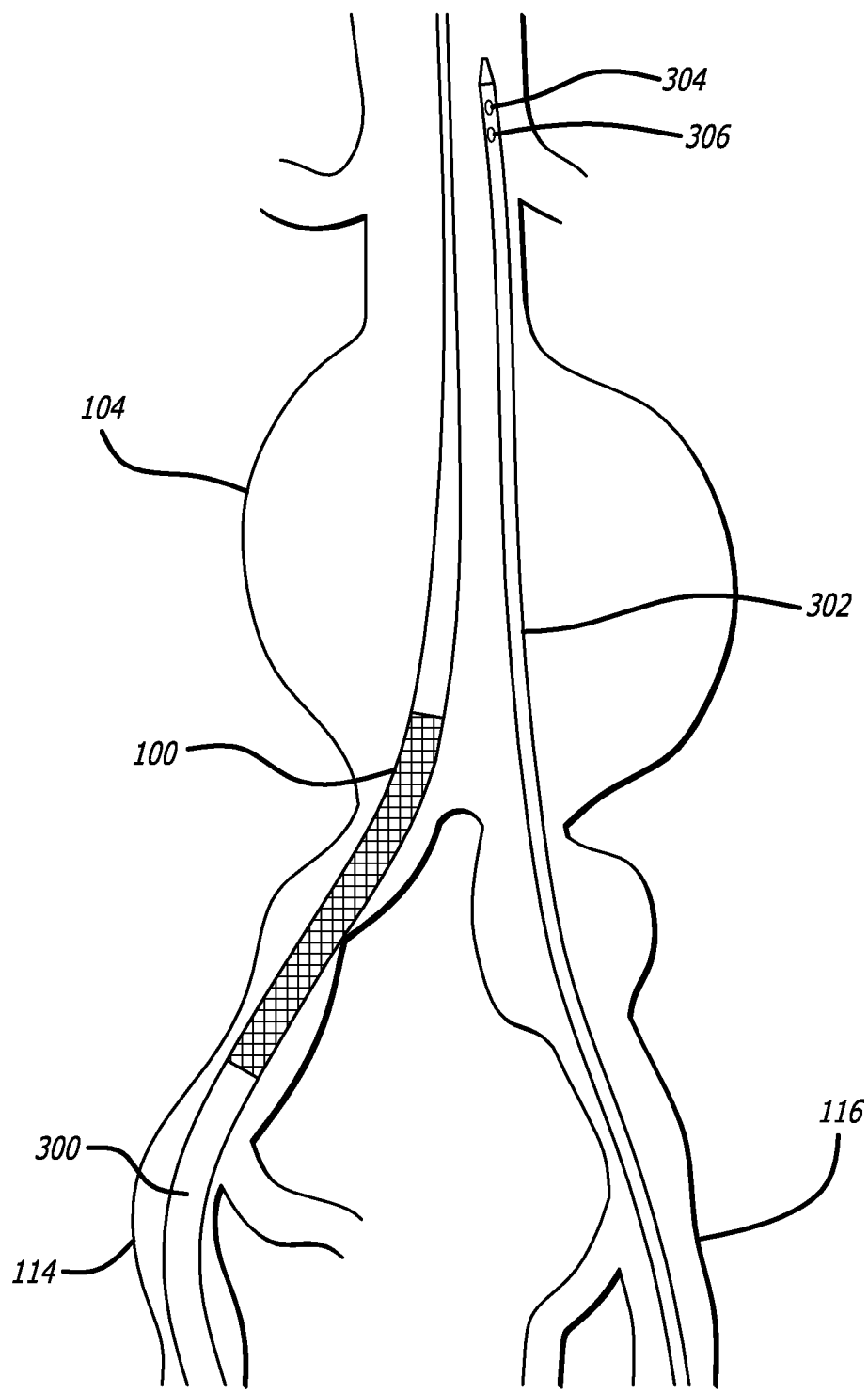
FIGS. 3a-c depict deployment of a stent graft and a multilumen injection catheter suitable for injection of a cell growth promoting factor during stent graft deployment.
Figure 3B:
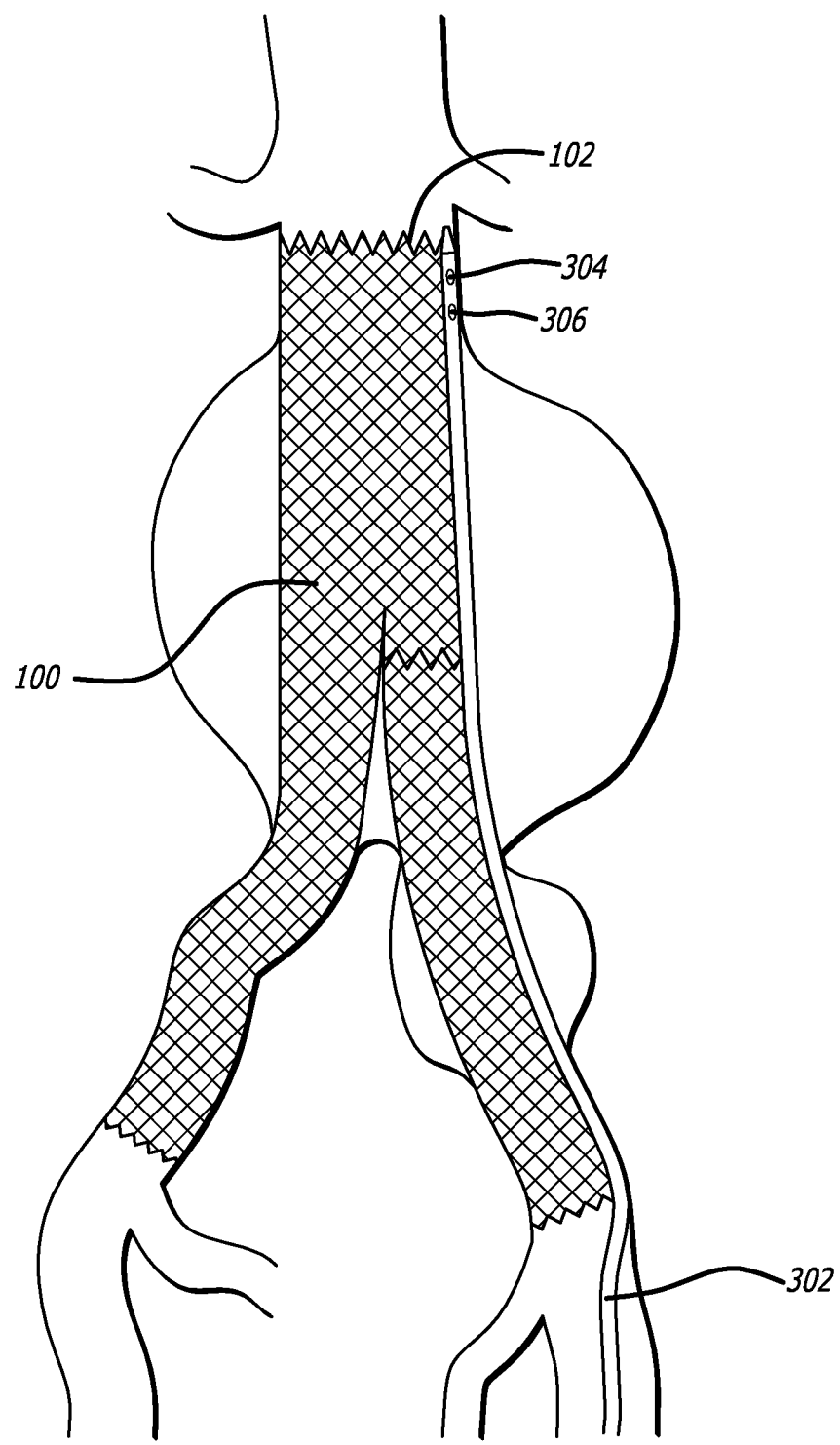
Figure 3C:
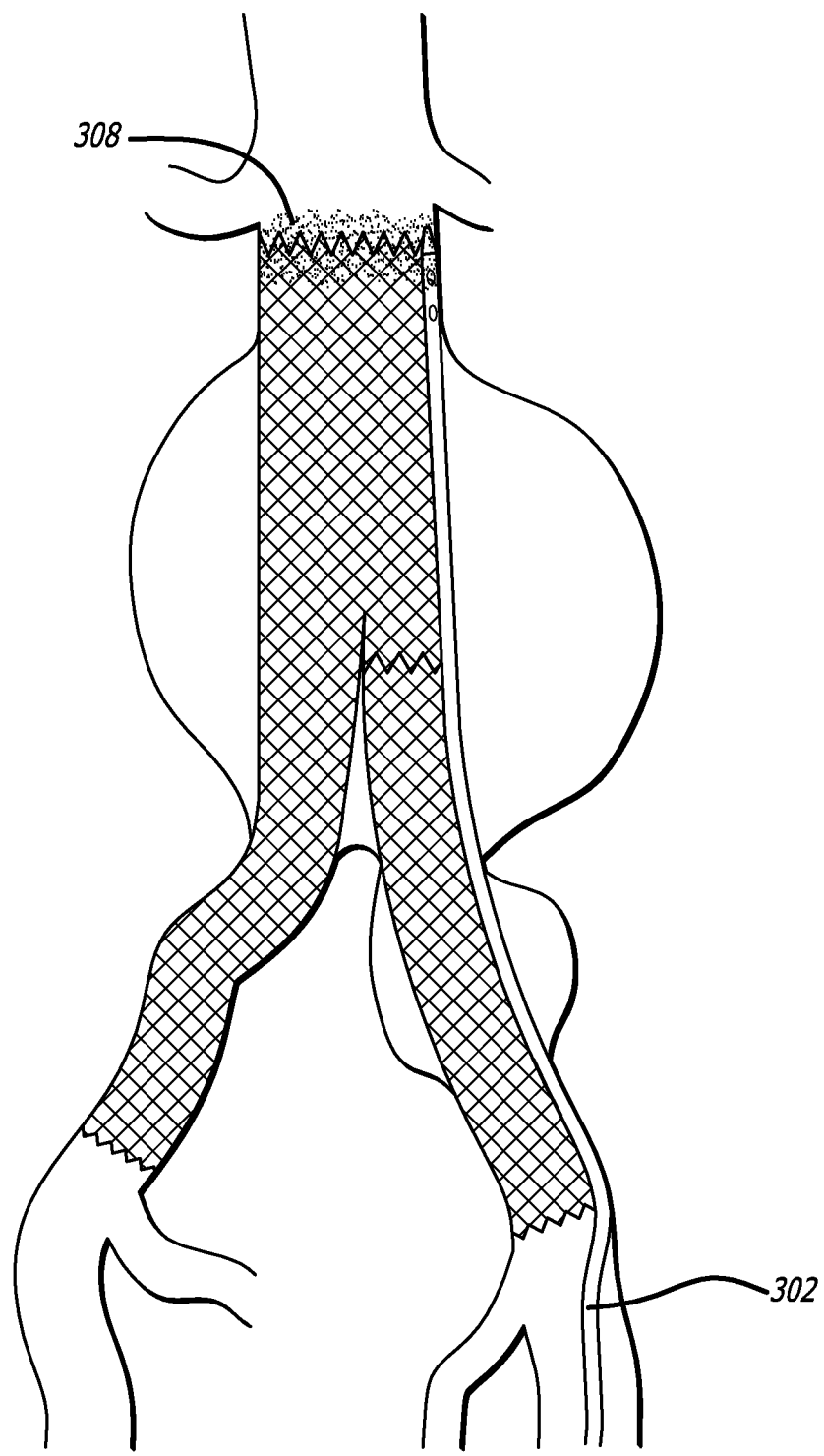

In another embodiment, APG or other substances can be injected (delivered) between the stent graft and the vessel wall during or after stent graft placement. As depicted in FIG. 3a, a bifurcated stent graft segment 100 is radially compressed and delivered to an aneurysm site 104 with delivery catheter 300 via the right iliac artery 114. A multilumen injection catheter 302 is also deployed to the treatment site through the left iliac artery 116. The multilumen injection catheter 302 can be a coaxial catheter with two injection lumens or a dual lumen catheter or alternatively a three lumen catheter if a guide wire lumen is required. Injection catheter 302 has injection (delivery) ports 304 and 306 through which PRP, thrombin or other substances can be deposited. In the first step of this deployment scheme (FIG. 3a), the stent delivery catheter 300 and the injection catheter 302 are deployed independently to the treatment site. After stent graft deployment, delivery catheters are removed while the injection catheter 302 remains in place (FIG. 3b) with its injection (delivery) ports 304 and 306 aligned with the distal end 102 of bifurcated stent graft segment 100. Thrombin, PRP or other substances are injected (delivered) (in one embodiment simultaneously) between the vessel lumen wall and the stent graft at the distal end 102 of bifurcated stent graft segment 100 to form APG 308 (FIG. 3c). The injection catheter 302 is then retrieved from the treatment site. This same procedure can be repeated as necessary to apply APG or other substances to the stent graft and/or luminal wall at other locations.

Figure 4A:
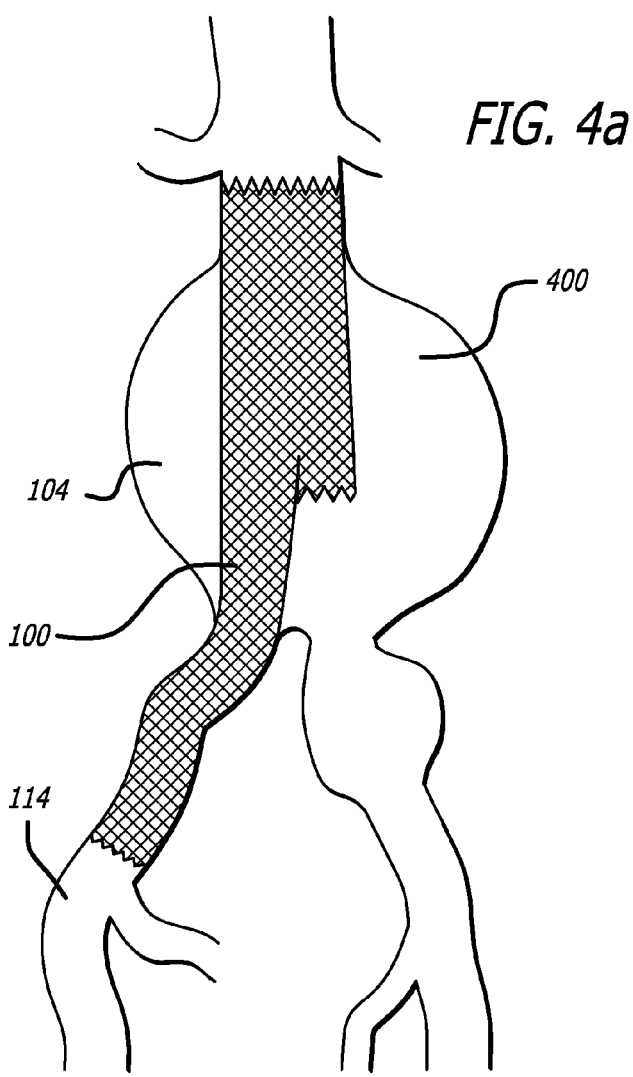
FIGS. 4a-d depict a method of injecting APG or other substances directly into an aneurysm sac after deployment of a stent graft.
Figure 4B:
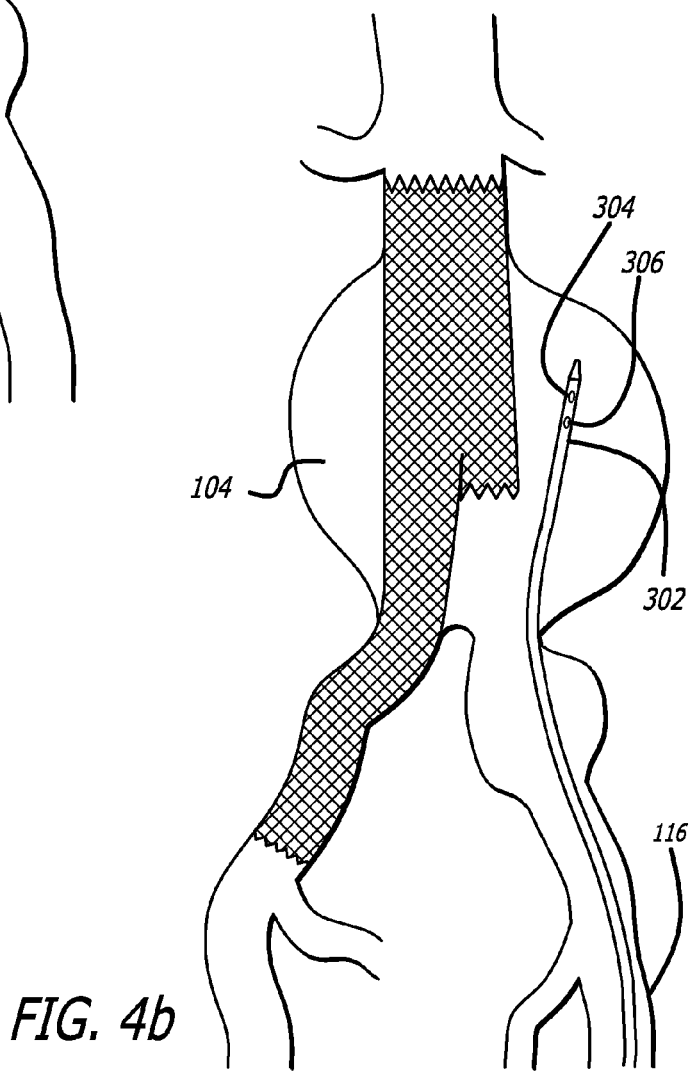
Figure 4C:
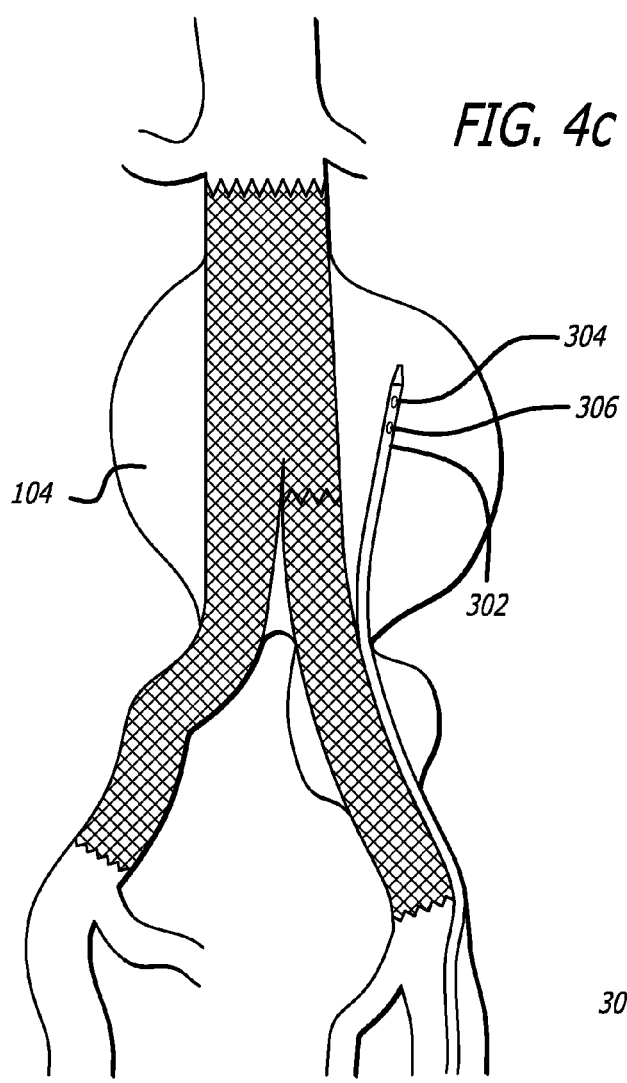
Figure 4D:
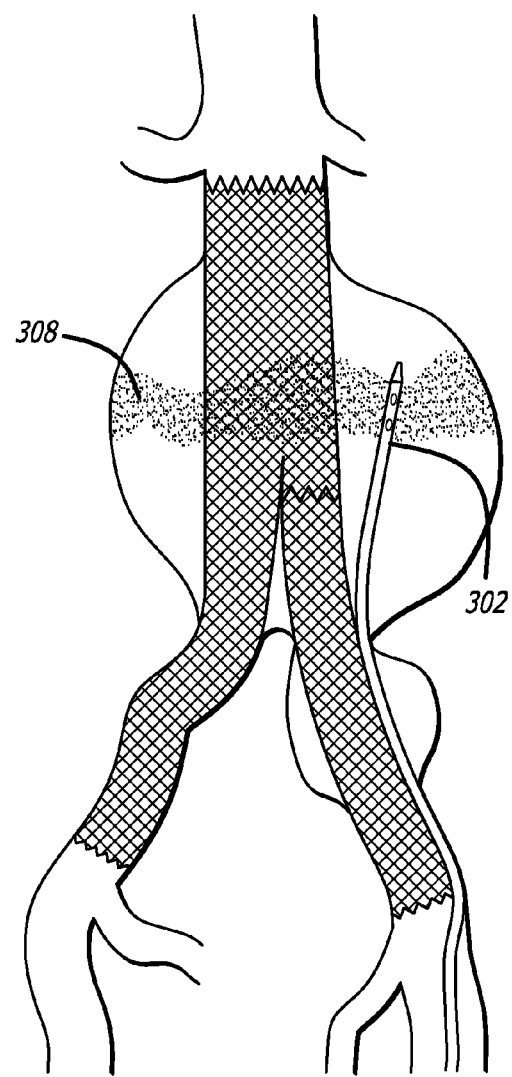

In another embodiment, APG and other substances can be delivered directly to the aneurysm sac. As previously described, bifurcated stent graft segment 100 is radially compressed to fill the stent graft chamber of a stent delivery catheter which is then deployed to the treatment site via the right iliac artery 114 (FIG. 4a). An injection catheter 302 is also deployed to the aneurysm sac 104 through the left iliac artery 116 (FIG. 4b). Again, the injection catheter 302 can be a coaxial catheter with two injection lumens or a dual lumen catheter or alternatively a three lumen catheter if a guide wire lumen is required. Injection catheter 302 has injection (delivery) ports 304 and 306 through which PRP, thrombin or other substances can be deposited. In FIG. 4c, the stent graft delivery catheters have been removed while the injection catheter 302 remains in place with its injection (delivery) ports 304 and 306 in the aneurysm sac 104. Thrombin, PRP or other substances can be injected (delivered) (in one embodiment simultaneously) between the vessel lumen wall and the stent graft within the aneurysm sac to form APG 308 (FIG. 4d). An amount of PRP and thrombin necessary to produce enough APG to fill the aneurysm sac is deployed. The injection catheter 302 is then removed from the site.

In another embodiment, single lumen injection catheters can be used in the place of the previously described multilumen injection catheter. After the guide wire is retrieved from the lumen, PRP, thrombin or other substances can be delivered to the treatment site sequentially through the same lumen of the single lumen injection catheter. In an alternate embodiment, more than one single lumen injection catheter can be deployed in each iliac artery with the distal ends of the catheters within the aneurysm sac. Substances can then each be injected (delivered) through the single lumen injection catheters to form APG in the aneurysm sac.

Figure 5A:
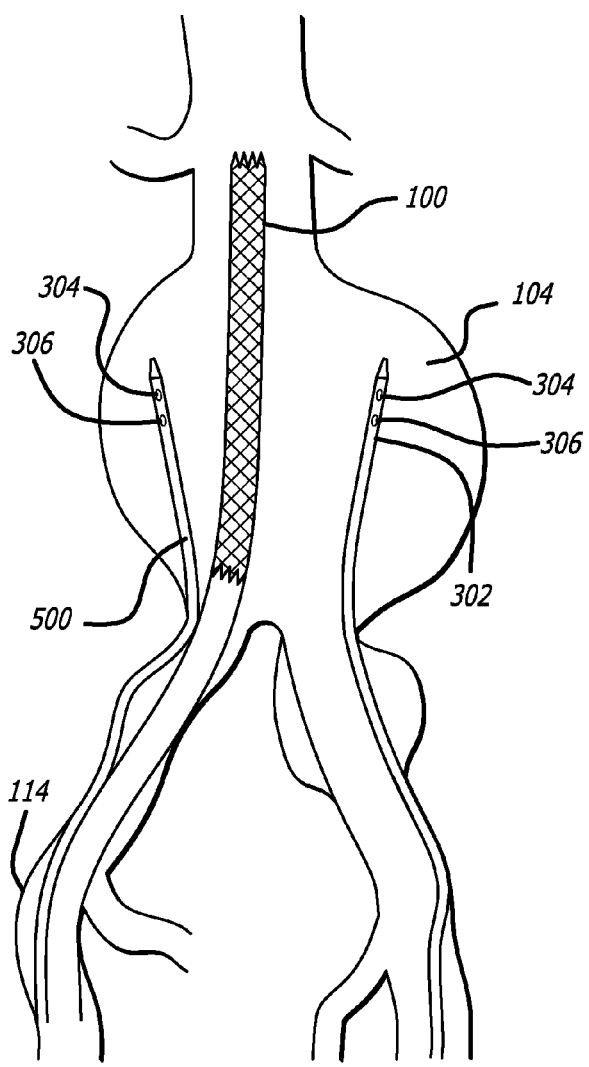
FIGS. 5a-c depict an alternate method of injection of APG or other substances directly into an aneurysm sac after deployment of a stent graft.
Figure 5B:
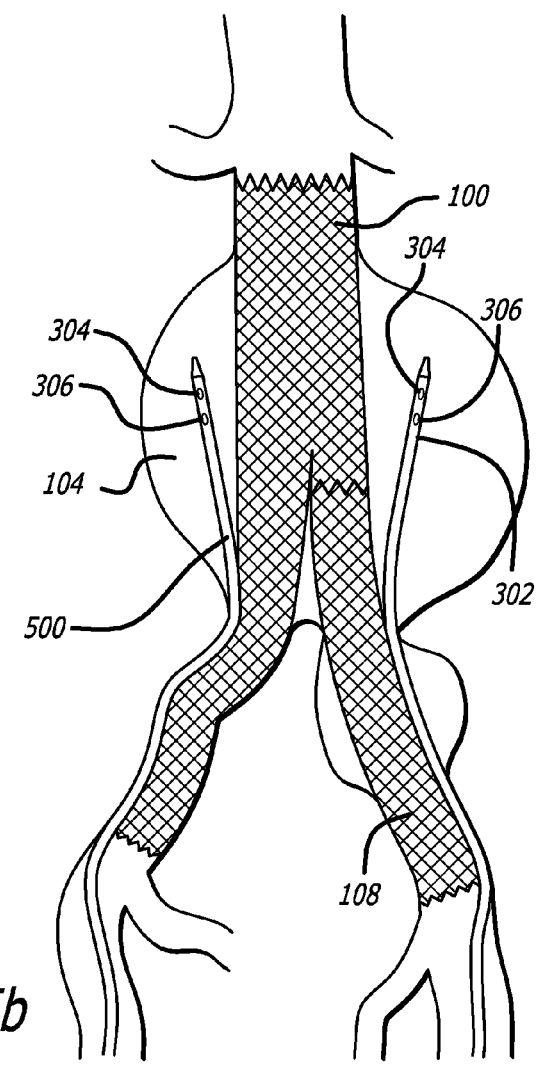
Figure 5C:
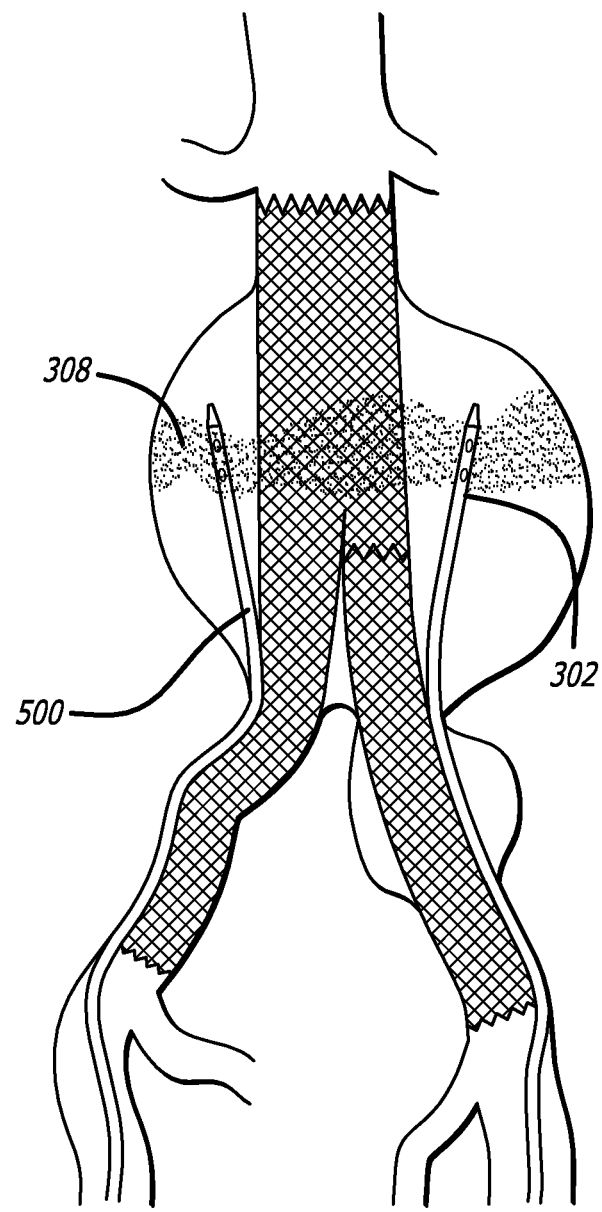

In an alternative embodiment, more than one injection catheter can be used to form APG within the aneurysm sac (FIG. 5). As previously described, bifurcated stent graft segment 100 is radially compressed to fill the stent graft chamber of a stent delivery catheter which is then deployed to the treatment site via the right iliac artery 114 (FIG. 5a). Multiple single lumen or multilumen injection catheters 302 and 500 are also deployed to the aneurysm sac through the right iliac artery 114 and/or left iliac artery. Injection catheters 302 and 500 have injection (delivery) ports 304, 306 through which PRP, thrombin or other substances can be deposited. The delivery catheter for bifurcated stent graft segment 100 is removed and the iliac limb segment 108 of bifurcated stent graft segment 100 is deployed as described in FIG. 1 while injection catheters 302 and 500 remain in place (FIG. 5b) with their injection (delivery) ports 304 and 306 in the aneurysm sac 104. The iliac limb segment of the stent graft seals the aneurysm sac at the proximal end. Thrombin, PRP or other substances are injected (delivered) simultaneously between the vessel lumen wall and the stent graft within the aneurysm sac to form APG 308 (FIG. 5c). An amount of PRP and thrombin necessary to produce enough APG to fill the aneurysm sac and seal the ends can be determined radiographically by measuring the size of the aneurysm sac prior to surgery. The injection catheters 302 and 500 are then retrieved.

Figure 6:
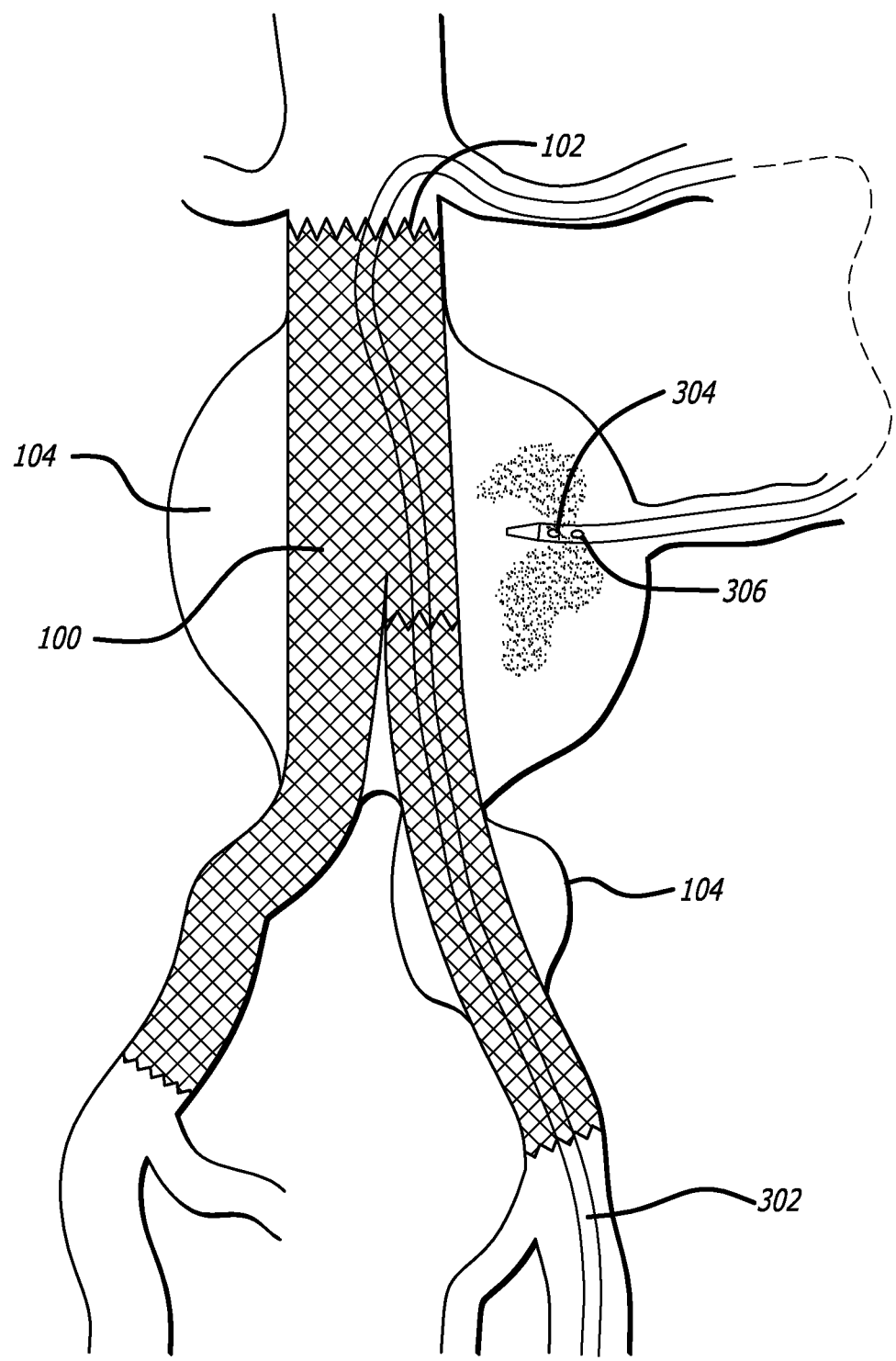
FIG. 6 depicts an alternate method of injection of APG or other substances directly into the aneurysm sac after deployment of a stent graft.

In yet another embodiment, depending on stent graft placement, a collateral artery can be used to access the luminal wall-contacting surface of a deployed bifurcated stent graft segment 100 (FIG. 6). For example, and not intended as a limitation, bifurcated stent graft segment 100 may be deployed such that the distal end 102 of the bifurcated stent graft segment 100 is in the abdominal aorta near, but below the renal artery. After deployment of bifurcated stent graft segment 100, the deployment catheter is removed and an injection catheter 302 is advanced up the aorta past the treatment site 104 to the superior mesenteric artery. The injection catheter 302 is then advanced through the superior mesenteric artery and down into the inferior mesenteric artery where it originates at the aorta at the treatment site 104 and proximal to the distal end of the stent graft 102. The APG constituents are then injected (delivered) through injection (delivery) ports 304, 306 at a site adjacent the lumen wall/stent graft interface or into the aneurysm sac 104 and allowed to diffuse into and around the stent graft.

Figure 13:
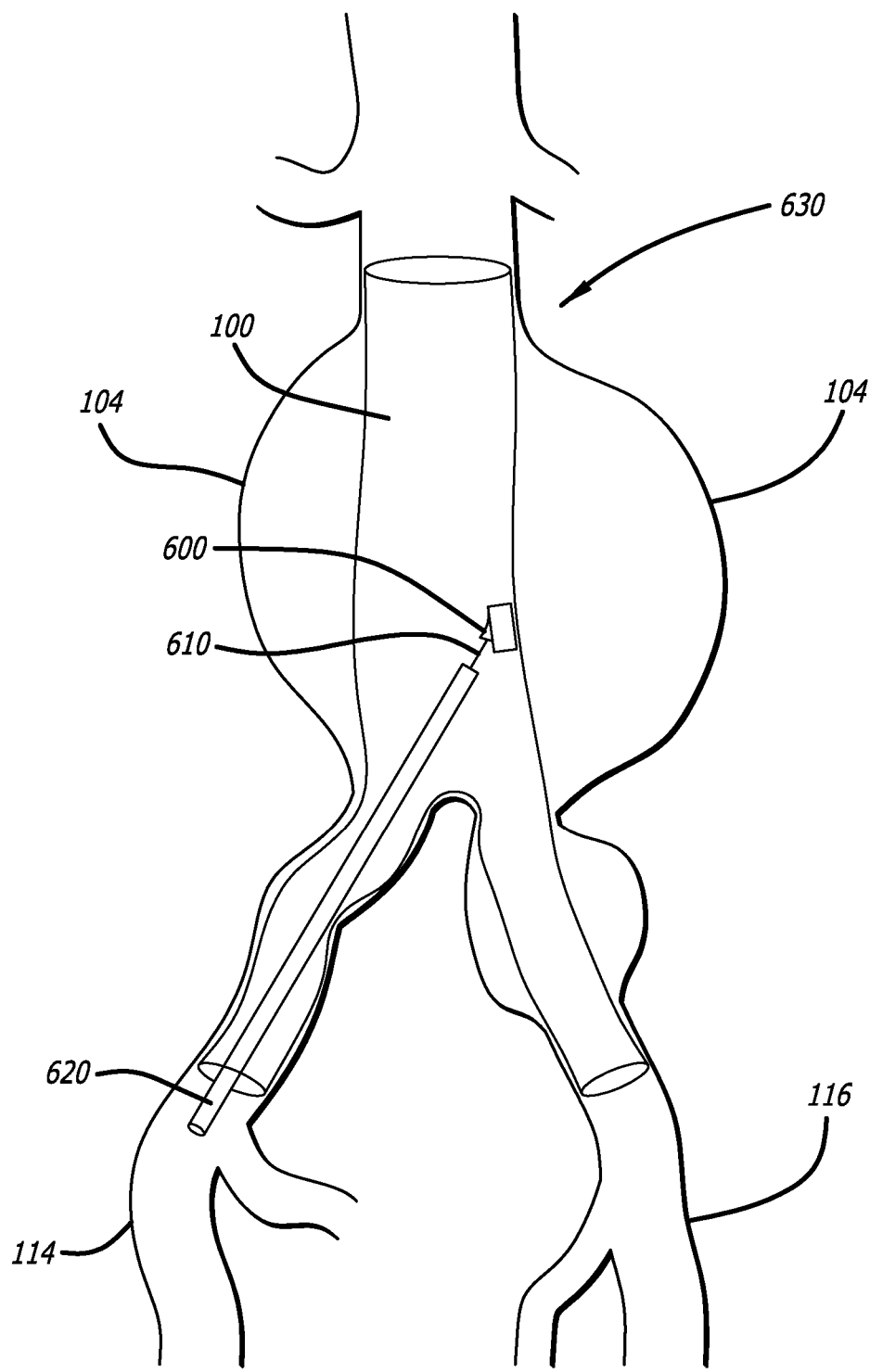
FIG. 13 depicts an alternate method of injection of APG or other substances directly into the aneurysm sac after deployment of a stent graft, through a port in the stent graft.

APG can also be placed into the aneurysmal sac 104 isolated behind stent graft by virtue of providing an alternative structure in the bifurcated stent graft segment 100, such that a port 600 is provided to provide access between the interior of the stent graft and the aneurysmal sac 104. Referring now to FIG. 13, bifurcated stent graft segment 100 is shown having a port 600 extending through the graft portion thereof, such that port 600 may be manipulated, by a hook 610 or other device on the end of a wire or catheter 620, between an open position (shown in FIG. 13) and a closed position (not shown). To place the APG into the isolated aneurysmal sac 100, port 600 is opened, such as by a locating a hook 610 adjacent thereto by introducing the hook on the end of a wire or of catheter 620, and using such hook to manipulate the port 600 open. The hook is then withdrawn into its own sheath in the end of catheter 620, or moved upwardly in aorta 630 to a non-interfering position with respect to port 600, and then an additional wire (not shown) is directed from catheter 620, holding the APG, or components thereof, therein, into aneurysmal sac 140. The APG is then injected (delivered) from catheter 620 and deposited in the aneurysmal sac 104, and the wire is withdrawn through port 600. Catheter 620 is then manipulated, in conjunction with hook 610, to position hook 610 to close port 600. Catheter 620 is then withdrawn from the body, and the incisions through which they were placed are closed.

Once the APG, or alternate cell growth promoting factor, or combinations thereof, has been administered to the stent graft/vessel lumen interface as described herein, cell growth will be activated and cells will proliferate and adhere to the stent graft (a condition or process referred to herein after as "tissue in-growth" or endothelialization) thus anchoring the stent graft securely to the vessel lumen and preventing stent graft migration. Moreover, tissue in-growth can also provide a seal between the distal end of the luminal wall contacting surface of stent graft or other locations at risk for endoleak.

The following examples illustrate one or more embodiments according to the invention.

EXAMPLE 1

Properties of Platelet Rich Plasma

Aliquots of human peripheral blood (30-60 mL) are passed through the Magellan® Autologous Platelet Separation System (the Magellan® system) and the concentrated, platelet-rich plasma fraction (PRP) assayed for platelets (PLT), white blood cells (WBC) and hematocrit (Hct) (Table 1). The Magellan® system concentrated platelets and white blood cells six-fold and three-fold respectively.

TABLE 1

Blood cell yields after passing through the Magellan ® system.

| Mean ± SD n = 19 | Initial Blood | PRP | Yield |
|---|---|---|---|
| PLT (x 1000/µL) | 220.03 ± 48.58 | 1344.89 ± 302.00 | 6.14 ± 0.73 |
| WBC (x 1000/µL) | 5.43 ± 1.43 | 17.04 ± 7.01 | 3.12 ± 0.90 |
| Hct (%) | 38.47 ± 2.95 | 6.81 ± 1.59 | |

Cell Yield = cell count in PRP/cell count in initial blood = [times baseline]

Additionally, PRP was assayed for levels of the endogenous growth factors platelet-derived growth factor (PDGF), transforming growth factor-beta (TGF-β), basic fibroblast growth factor (bFGF), vascular endothelial growth factor (VEGF), and endothelial growth factor (EGF). As a result of increased platelet and white blood cell counts in PRP, increased concentrations of growth factors were found.

TABLE 2

Growth Factor Content of Blood and PRP

| Mean ± SD; n = 9 | Initial Blood | PRP |
|---|---|---|
| PDGF-AB (ng/mL) | 10.2 ± 1.4 | 88.4 ± 28.8 |
| PDGF-AA (ng/mL) | 2.7 ± 0.5 | 22.2 ± 4.2 |
| PDGF-BB (ng/mL) | 5.8 ± 1.4 | 57.8 ± 36.6 |
| TGF-β1 (ng/mL) | 41.8 ± 9.5 | 231.6 ± 49.1 |
| bFGF (pg/mL) | 10.7 ± 2.9 | 48.4 ± 25.0 |
| VEGF (pg/mL) | 83.1 ± 65.5 | 597.4 ± 431.4 |
| EGF (pg/mL) | 12.9 ± 6.2 | 163.3 ± 49.4 |

EXAMPLE 2

Autologous Platelet Gel Generation

Autologous Platelet Gel (APG) is generated from the PRP fraction produced in the Magellan® system by adding thrombin and calcium to activate the fibrinogen present in the PRP. For each approximately 11 mL of PRP (or PPP), approximately 1000 units of bovine thrombin in 1 mL 10% calcium chloride (a 1:11 ratio of thrombin:PRP) are required for activation. Alternatively, if autologous thrombin is used, the amount of thrombin is approximately 12 NIH units mixed with 3.3 mL PRP (1:3.3 ratio of thrombin:PRP). The APG is formed immediately upon mixing of the activator solution with the PRP. The concentration of thrombin can be varied from approximately 1-1,000 U/mL, depending on the speed required for setting to occur. The lower concentrations of thrombin will provide slower gelling times.

EXAMPLE 3

Effects of APG on Cell Proliferation

A series of in vitro experiments were conducted evaluating the effect of released factors from APG on the proliferation of the human microvascular endothelial cells, human coronary artery smooth muscle cells and human dermal fibroblasts. Primary cell cultures of the three cell types were established according to protocols well known to those skilled in the art of cell culture. For each cell type, three culture conditions were evaluated. For APG cultures, APG was added to cells in basal medium. A second group of cells were cultured in growth medium. Growth medium is the standard culture medium for the cell type and contains optimal growth factors and supplements. The control cultures contain cells cultured only in basal medium which contains no growth factors.

Figure 7:
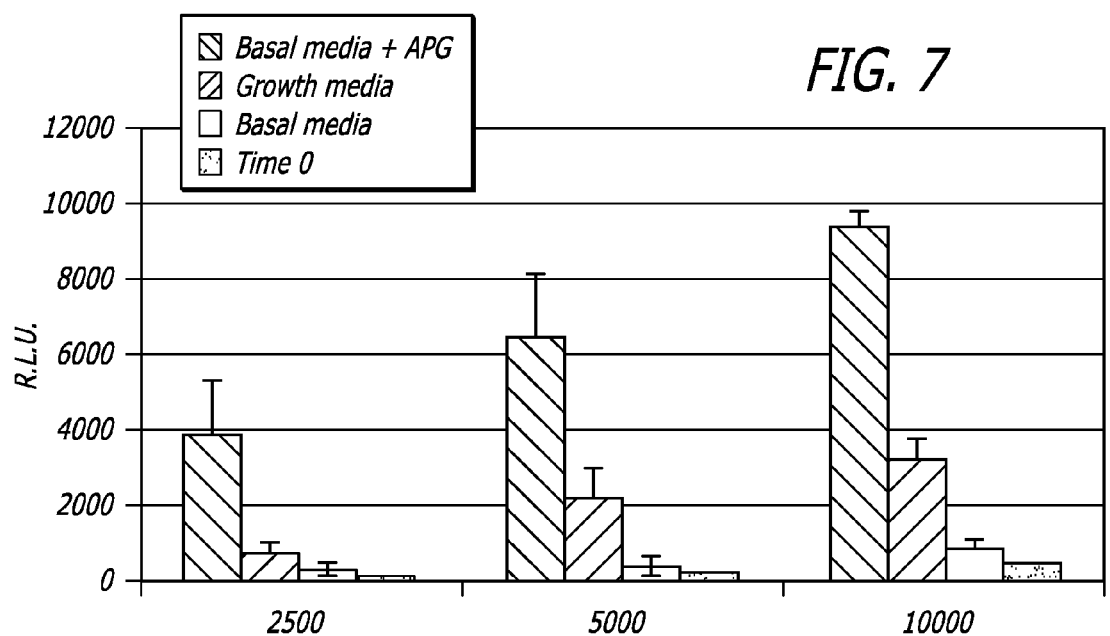
FIG. 7 depicts the effects of the APG on arterial smooth muscle cell proliferation.
Figure 8:
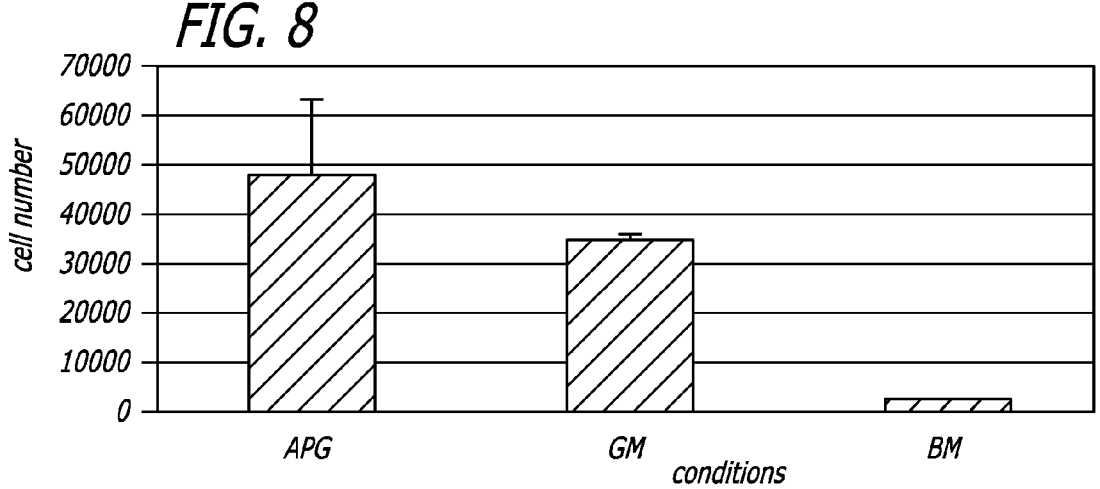
FIG. 8 depicts the effects of the APG on endothelial cell proliferation.
Figure 9:
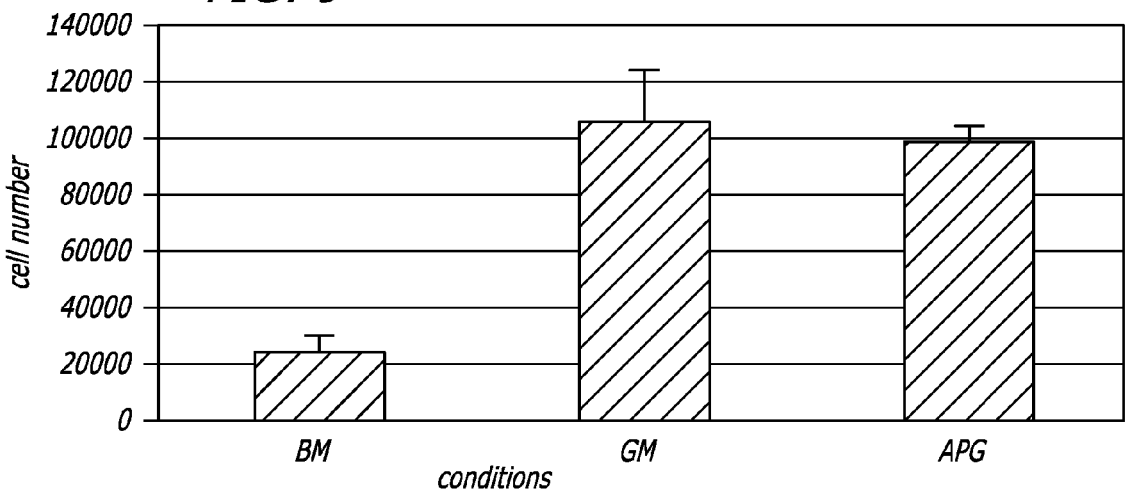
FIG. 9 depicts the effects of the APG on fibroblast cell proliferation.

Autologous platelet gel had a significant growth effect on human coronary artery smooth muscle cells after five days of culture (FIG. 7), human microvascular endothelial cells after four days of culture (FIG. 8) and on human dermal fibroblasts after five days of culture (FIG. 9).

EXAMPLE 4

Effect of Platelet Poor Plasma on Human Dermal Fibroblast Growth

In addition to the platelet-rich plasma fraction, the Magellan® system generates a platelet-poor plasma (PPP) fraction as well. This PPP fraction was further processed by centrifuging at 10,000×g for 10 minutes to produce a supernatant essentially free of platelets. The supernatant was then activated with the $CaCl_2$/thrombin activator solution used in the APG generation. Human dermal fibroblasts were then cultured in basal medium containing PRP gel or PPP gel. Culture conditions for proliferation of human dermal fibroblasts are well known to those of ordinary skill in the art of cell culture.

Figure 10:
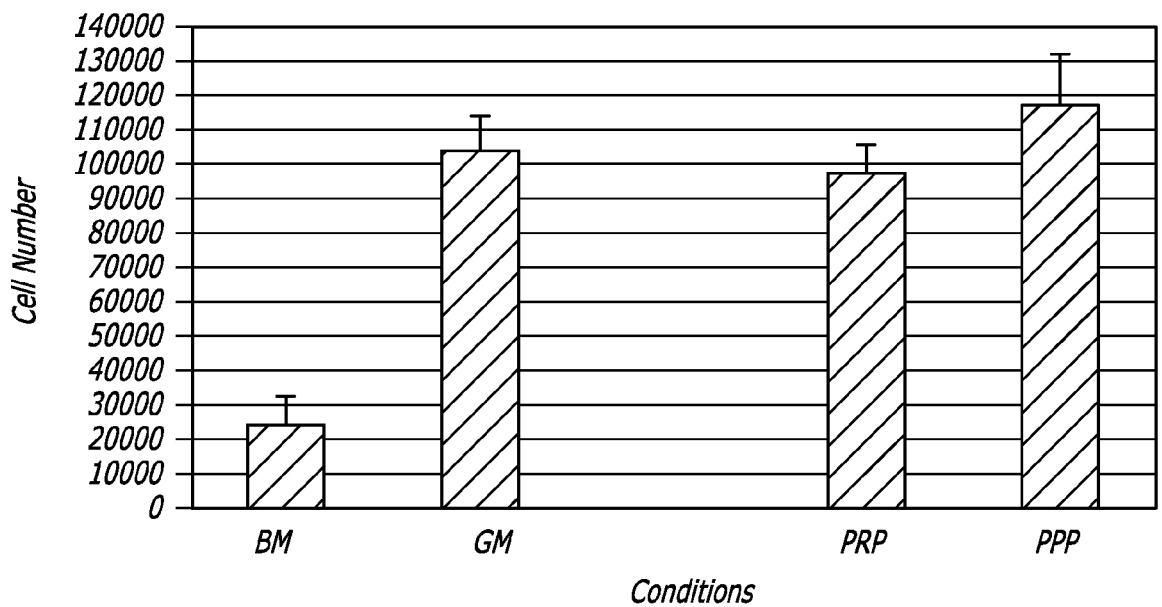
FIG. 10 depicts the effects of platelet poor plasma (PPP) on human dermal fibroblast growth.

Human dermal fibroblasts cultured in the presence of PPP gel proliferated to a similar extent as those cultured in the presence of PRP gel (FIG. 10).

EXAMPLE 5

Effect of APG on Endothelial Cell Migration

Figure 11:
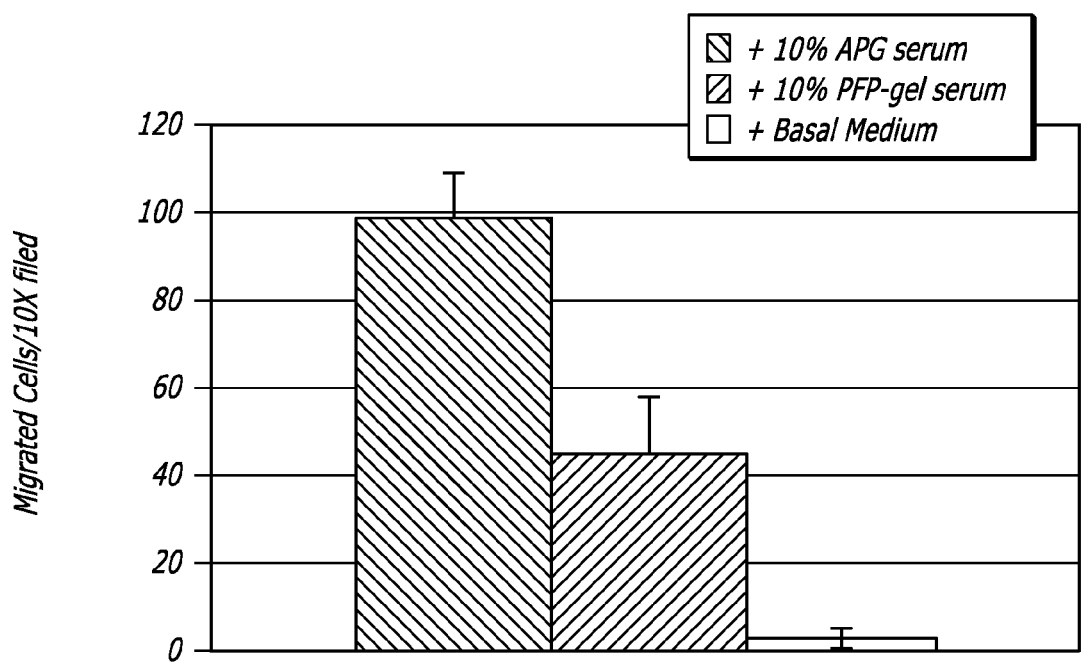
FIG. 11 depicts the effects of the APG on endothelial cell migration.

Human microvascular endothelial cell migration was performed in a Boyden chemotaxis chamber which allows cells to migrate through 8 μm pore size polycarbonate membranes in response to a chemotactic gradient. Human microvascular endothelial cells ($5 \times 10^5$) were trypsinized, washed and resuspended in serum-free medium (DMEM) and 400 μL of this suspension was added to the upper chamber of the chemotaxis assembly. The lower chamber was filled with 250 μL serum-free DMEM containing either 10% APG-derived serum, 10% platelet-free plasma (PFP)-derived serum or DMEM alone. After a pre-determined amount of time, the filters were removed and the cells remaining on the upper surface of the membrane (cells that had not migrated through the filter) were removed with a cotton swab. The membranes were then sequentially fixed, stained and rinsed to enable the visualization and quantification of cells that had migrated through the pores to the other side of the membrane. Autologous platelet gel-derived serum induced significantly more migration in human microvascular endothelial cells than either PFP or basal medium (FIG. 11).

EXAMPLE 6

Effect of APG on Neovascularization in Athymic Mice

Autologous platelet gel was injected subcutaneously in nude (athymic) mice to determine if the APG is detectable and retrievable after a seven day implantation period. Athymic mice were injected with 500 μL of either APG or an inert Matrigel® biological cell culture substrate control. Each animal was injected with Matrigel® biological cell culture substrate in the left flank and APG in the right flank. After seven days the implants and the surrounding tissue were subjected to histological analysis (FIG. 12). In the area of the Matrigel® biological cell culture substrate control implant there was minimal reaction to the material and a very thin capsule of loose connective tissue rimmed the mass (FIG. 12a). In the area of the APG implant, the APG was deeply infiltrated by spindle shaped cells (fibroblasts and macrophages) along with moderate numbers of neutrophils (FIG. 12b). The entire mass was rimmed by a thick layer of fibrovascular tissue and the tissue showed significant neovascularization.

Endothelialization has been observed to naturally occur in few human coronary stents within weeks of implantation. This natural endothelialization is not complete or consistent, however, and does not prevent the stent graft side effects of graft migration and endoleak. Methods to increase endothelialization are sought to improve clinical outcome after stent grafting.

Endothelialization may be stimulated by induced angiogenesis resulting in formation of new capillaries in the interstitial space and surface endothelialization. This has led to modification of medical devices with vascular endothelial growth factor (VEGF) and fibroblast growth factors 1 and 2 (FGF-1, FGF-2). The discussion of these factors is for exemplary purposes only, as those of skill in the art will recognize that numerous other growth factors have the potential to induce cell-specific endothelialization. VEGF is endothelial cell-specific however it is a relatively weak endothelial cell mitogen. FGF-1 and FGF-2 are more potent mitogens but are less cell specific. The development of genetically-engineered growth factors is anticipated to yield more potent endothelial cell-specific growth factors. Additionally it may be possible to identify small molecule drugs that can induce endothelialization.

Unless otherwise indicated, all numbers expressing quantities of ingredients, properties such as molecular weight, reaction conditions, and so forth used in the specification are to be understood as being modified in all instances by the term "about." Accordingly, unless indicated to the contrary, the numerical parameters set forth in the following specification are approximations that may vary depending upon the desired properties sought to be obtained. Notwithstanding that the numerical ranges and parameters are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended to better illuminate embodiments according to the invention.

Groupings of alternative elements or embodiments according to the invention disclosed herein are not to be construed as limitations. Each group member may be referred to individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Embodiments according to this invention are described herein. Of course, variations on those embodiments will become apparent to those of ordinary skill in the art upon reading the foregoing description unless otherwise indicated herein or otherwise clearly contradicted by context.

Furthermore, numerous references have been made to patents and printed publications throughout this specification. Each of the above cited references and printed publications are individually incorporated herein by reference in their entirety.

What is claimed is:

1. A method of treating an aneurysm sac comprising
   mixing platelet rich plasma (PRP) with thrombin to form a gel ex vivo;
   allowing the gel to retract such that a growth factor-rich exudate is formed from the retracted gel;
   collecting said growth factor rich exudate from the retracted gel;
   mixing said collected growth factor rich exudate with platelet poor plasma (PPP) to form a mixture; and then
   injecting said mixture into an aneurysm sac simultaneously with thrombin to form a non-retractable gel.

2. The method of claim 1 wherein said method further comprises the step of implanting a stent graft.

3. The method of claim 2 wherein said stent graft is implanted prior to injecting said mixture into said aneurysm sac.

4. The method of claim 2 wherein said mixture is injected between said stent graft and said aneurysm sac.

* * * * *